United States Patent
Kraft et al.

(10) Patent No.: US 8,182,781 B2
(45) Date of Patent: May 22, 2012

(54) ALPHA-SILYL ALCOHOLS POSSESSING OLFACTORY PROPERTIES REMINISCENT OF PATCHOULI OIL

(75) Inventors: Philip Kraft, Dübendorf (CH); Astrid Sunderkötter, Göttingen (DE); Reinhold Tacke, Würzburg (DE)

(73) Assignee: Givaudan S.A., Vernier (CH)

( * ) Notice: Subject to any disclaimer, the term of this patent is extended or adjusted under 35 U.S.C. 154(b) by 0 days.

(21) Appl. No.: 13/265,096

(22) PCT Filed: Apr. 19, 2010

(86) PCT No.: PCT/EP2010/055089
§ 371 (c)(1),
(2), (4) Date: Oct. 18, 2011

(87) PCT Pub. No.: WO2010/121979
PCT Pub. Date: Oct. 28, 2010

(65) Prior Publication Data
US 2012/0040879 A1      Feb. 16, 2012

(30) Foreign Application Priority Data

Apr. 20, 2009 (GB) .................................. 0906756.2

(51) Int. Cl.
*A61K 8/00* (2006.01)
*C07F 7/08* (2006.01)
(52) U.S. Cl. ........................... 423/325; 512/1; 568/700
(58) Field of Classification Search ................ 423/325; 512/1; 568/700
See application file for complete search history.

(56) References Cited

U.S. PATENT DOCUMENTS

| | | | |
|---|---|---|---|
| 4,916,247 A * | 4/1990 | Steinmann | 556/82 |
| 4,965,316 A * | 10/1990 | Steinmann | 525/100 |
| 6,051,362 A * | 4/2000 | Choi et al. | 430/270.1 |
| 6,607,867 B1 | 8/2003 | Kim et al. | |

OTHER PUBLICATIONS

GB 0906756.2—Great Britain Search Report, Jul. 7, 2009.
PCT/CH2010/055089—Written Opinion of the International Searching Authority, Jun. 18, 2010.
PCT/CH2010/055089—International Search Report, Jun. 18, 2010.
Rempfer, Beate, et al., "The (p-d).pi.bonding in Fluorosilanes? Gas-phase structures of (CH3)4-nSiFn with n=1-3 and of (tert-BU)2SiF2", Journal of the American Chemical Society, 1986, vol. 108, No. 14, pp. 3893-3897.
Gilman, Henry, "The Synthesis and Some Reactions of α-Silylcarbinols", Journal of the American Chemical Society, 1958, vol. 80, pp. 2680-2682.
Dunogues, Jacques, et al., "Direct C-Silylation of Acetone Using Trimethylchlorosilane", Journal of Organometallic Chemistry, 1973, vol. 49, No. 1, pp. c9-c12.
Dunogues, Jacques, et al., "Nouvelle Methode de C-Silylation Directe de Centones Saturees ou α-Ethyleniques", Journal of Organometallic Chemistry, 1987, vol. 87, No. 2, pp. 151-167, XP-2585328.
Aizpura, J.M., et al, "Product Subclass 28: α-Silyl Alcohols, ethers and Amines", Science of Synthesis, Jan. 1, 2002, vol. 4, pp. 595-632, XP-009087055.
Soderquist, John A., et al., "Hydroboration. 56. Convenient and Regiospecific Route to Functionalized Organosilanes Through the Hydroboration of Alkenylsilanes", Journal of Organic Chemistry, 1980, vol. 45, pp. 3571-3578.
Kayed, Hany, et al., "FXYD3 is Overexpressed in Pancreatic Ductal Adenocarcinoma and Influences Pancreatic Cancer Cell Growth", International Journal of Cancer, 2006, vol. 118, pp. 43-54, XP-002585328.

* cited by examiner

*Primary Examiner* — John Hardee
(74) *Attorney, Agent, or Firm* — Curatolo Sidoti Co., LPA; Joseph G. Curatolo; Salvatore A. Sidoti

(57) ABSTRACT

The present disclosure refers to sila-substituted carbinols of formula (I)

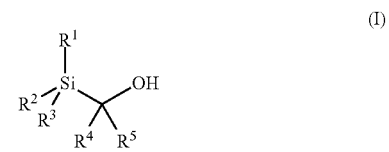

wherein $R^1$, $R^2$ and $R^3$ are independently selected from $C_1$-$C_4$ alkyl or $C_3$-$C_4$ cycloalkyl; $R^4$ is methyl or ethyl; and $R^5$ is methyl or ethyl. The disclosure further refers to their preparation and to perfume compositions and fragrance applications comprising them.

10 Claims, No Drawings

ALPHA-SILYL ALCOHOLS POSSESSING OLFACTORY PROPERTIES REMINISCENT OF PATCHOULI OIL

CROSS REFERENCE TO RELATED APPLICATIONS

This application is a national stage application of International Application No. PCT/EP2010/055089, filed 19 Apr. 2010, which claims priority from Great Britain Patent Application Serial No. 0906756.2, filed 20 Apr. 2009, from which applications priority is claimed, and which are incorporated herein by reference.

The present invention relates to novel compounds possessing olfactory properties reminiscent of patchouli oil. The invention furthermore refers to a method for their production and to flavour and fragrance compositions containing these.

With its powerful and well-balanced woody, earthy, camphoraceous and floral facets patchouli oil constitutes one of the most important natural raw materials in perfumery. The principal odorant of patchouli oil is the tricyclic sesquiterpene (−)-patchoulol, which can reach levels of up to 40% in the essential oil. It is however structurally too complex to allow a synthetic approach that could compete with the price of the natural material. Thus, there is an ongoing demand in the fragrance and flavour industry for new compounds imparting, enhancing, or improving patchouli-like odour notes.

We have now found a novel class of sila-substituted carbinols that possess very natural patchouli odours, some of which closely reminiscent to the natural oil.

Accordingly, in a first embodiment, there is provided the use as fragrance of a compound of formula (I)

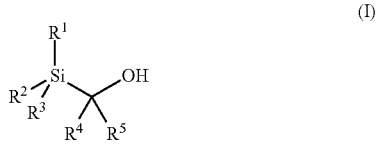
(I)

wherein
$R^1$, $R^2$ and $R^3$ are independently selected from $C_1$-$C_4$ alkyl (methyl, ethyl, propyl, isopropyl, isobutyl, tert.-butyl) and $C_3$-$C_4$ cycloalkyl (e.g. cyclopropyl); with the proviso that at least one of $R^1$, $R^2$ and $R^3$ is selected from $C_3$-$C_4$ alkyl (e.g. isopropyl) or $C_3$-$C_4$ cycloalkyl (e.g. cyclopropyl);
$R^4$ is methyl or ethyl; and
$R^5$ is methyl or ethyl.

When $R^1$ and $R^2$ and $R^3$ are different from one another, or when $R^4$ and $R^5$ are different from one another, stereocenters arise, which lead to different enantiomers. When $R^1$ and $R^2$ and $R^3$ are different from one another and $R^4$ and $R^5$ are different from one another as well, diastereomers are formed. The compounds of this invention can be used as stereoisomeric mixtures, or may be resolved in diastereomerically and/or enantiomerically pure form. Resolving stereoisomers adds to the complexity of manufacture and purification of these compounds, and so it is preferred to use the compounds as mixtures of their stereoisomers simply for economic reasons. However, if it is desired to prepare individual stereoisomers, this may be achieved according to methodology known in the art, e.g. by stereoselective synthesis or by preparative HPLC and GC.

Further non-limiting examples are compounds of formula (I) wherein at least two of $R^1$, $R^2$ and $R^3$ are selected from $C_3$-$C_4$ alkyl or $C_3$-$C_4$ cycloalkyl.

Further non-limiting examples are compounds of formula (I) wherein $R^4$ and $R^5$ are methyl.

Further non-limiting examples are compounds of formula (I) wherein $R^2$ and $R^3$ are independently selected from cyclopropyl and isopropyl.

In particular embodiments compounds of formula (I) selected from the group consisting of dicyclopropyl(1-hydroxy-1-methylethyl)methylsilane (1), tricyclopropyl(1-hydroxy-1-methylethyl)silane (2), dicyclopropyl(ethyl)(1-hydroxy-1-methylethyl)silane (3), dicyclopropyl(1-hydroxy-1-methylethyl)isopropylsilane (4), dicyclopropyl(1-hydroxy-1-methylpropyl)methylsilane (5), dicyclopropyl(1-ethyl-1-hydroxypropyl)methylsilane (6), (1-hydroxy-1-methylethyl)(diisopropyl)methylsilane (7), cyclopropyl(1-hydroxy-1-methylethyl)(diisopropyl)silane (8), (1-hydroxy-1-methylethyl)triisopropylsilane (9), (1-hydroxy-1-methylethyl)(isobutyl)isopropyl(methyl)silane (10), di-tert-butyl(1-hydroxy-1-methylethyl)methylsilane (11) and tert-butyl(1-hydroxy-1-methylethyl)dimethylsilane (12).

As used herein, the term "a compound of formula (I)" may refer to both a racemic mixture and the individually isolated isomers.

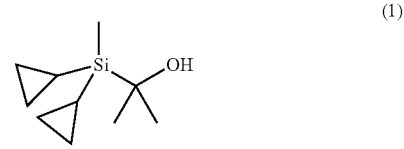
(1)

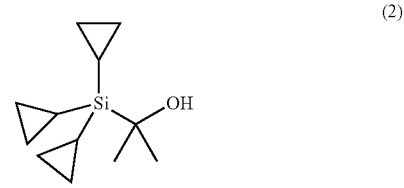
(2)

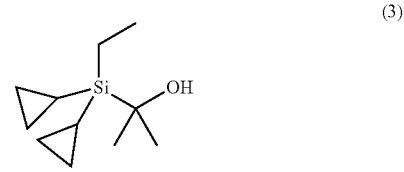
(3)

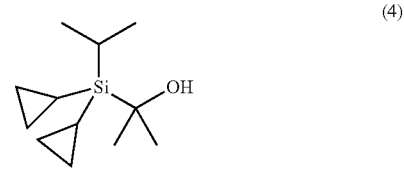
(4)

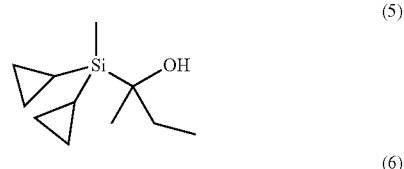
(5)

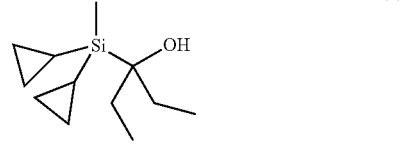
(6)

-continued

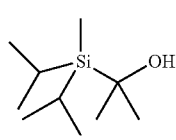

(7)

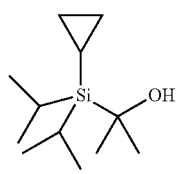

(8)

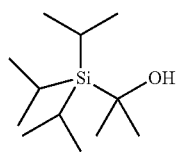

(9)

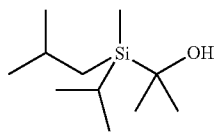

(10)

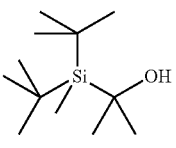

(11)

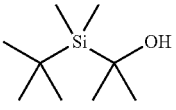

(12)

The compounds of formula (I) may be used alone, as mixtures thereof, or in combination with a base material. As used herein, the "base material" includes all known odorant molecules selected from the extensive range of natural products and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odorants in fragrance compositions, for example, carrier materials, and other auxiliary agents commonly used in the art.

As used herein, "fragrance composition" means any composition comprising at least one compound of formula (I) and a base material, e.g. a diluent conventionally used in conjunction with odorants, such as dipropyleneglycol (DPG), isopropylmyristate (IPM), triethylcitrate (TEC) and alcohol (e.g. ethanol).

The following list comprises examples of known odorant molecules, which may be combined with the compounds of the present invention:
  essential oils and extracts, e.g. castoreum, costus root oil, oak moss absolute, geranium oil, tree moss absolute, basil oil, fruit oils such as bergamot oil and mandarine oil, myrtle oil, palmarose oil, patchouli oil, petitgrain oil, jasmine oil, rose oil, sandalwood oil, wormwood oil, lavender oil or ylang-ylang oil;
  alcohols, e.g. cinnamic alcohol, cis-3-hexenol, citronellol, Ebanol™, eugenol, farnesol, geraniol, Super Muguet™, linalool, menthol, nerol, phenylethyl alcohol, rhodinol, Sandalore™, terpineol or Timberol™;
  aldehydes and ketones, e.g. Azurone® (7-(3-methylbutyl)-1,5-benzodioxepin-3-one), anisaldehyde, α-amylcinnamaldehyde, Georgywood™, hydroxycitronellal, Iso E® Super, Isoraldeine®, Hedione®, Lilial®, maltol, methyl cedryl ketone, methylionone, verbenone or vanillin;
  ethers and acetals, e.g. Ambrox™, geranyl methyl ether, rose oxide or Spirambrene™;
  esters and lactones, e.g. benzyl acetate, Cedryl acetate, γ-decalactone, Helvetolide®, γ-undecalactone or vetivenyl acetate;
  macrocycles, e.g. Ambrettolide, ethylene brassylate or Exaltolide®;
  heterocycles, e.g. isobutylquinoline.

The compounds according to formula (I) may be used in a broad range of fragrance applications, e.g. in any field of fine and functional perfumery, such as perfumes, air care products, household products, laundry products, body care products and cosmetics. The compounds can be employed in widely varying amounts, depending upon the specific application and on the nature and quantity of other odourant ingredients. The proportion is typically from 0.1 to 10 weight percent of the application. In one embodiment, compounds of the present invention may be employed in a fabric softener in an amount of from 0.001 to 0.1 weight percent. In another embodiment, compounds of the present invention may be used in fine perfumery in amounts of from 0.01 to 20 weight percent (e.g. up to about 10 weight percent), more preferably between 0.01 and 5 weight percent. However, these values are given only by way of example, since the experienced perfumer may also achieve effects or may create novel accords with lower or higher concentrations.

The compounds as described hereinabove may be employed in a consumer product base simply by directly mixing at least one compound of formula (I), or a fragrance composition with the consumer product base, or they may, in an earlier step, be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the consumer product base.

Thus, the invention additionally provides a method of manufacturing a fragrance application, comprising the incorporation of a compound of formula (I), as a fragrance ingredient, either by directly admixing the compound to the consumer product base or by admixing a fragrance composition comprising a compound of formula (I), which may then be mixed with a consumer product base, using conventional techniques and methods. Through the addition of an olfactory acceptable amount of at least one compound of the present invention as hereinabove described the odour notes of a consumer product base will be improved, enhanced or modified.

Thus, the invention furthermore provides a method for improving, enhancing or modifying a consumer product base by means of the addition thereto of an olfactorily acceptable amount of at least one compound of formula (I).

The invention also provides a fragrance application comprising:
  a) as odorant at least one compound of formula (I); and
  b) a consumer product base.

As used herein, "consumer product base" means a composition for use as a consumer product to fulfill specific actions, such as cleaning, softening, and caring or the like. Examples of such products include fine perfumery, e.g. perfume and eau de toilette; fabric care, household products and personal care products such as laundry care detergents, rinse conditioner, personal cleansing composition, detergent for dishwasher, surface cleaner; laundry products, e.g. softener, bleach, detergent; body-care products, e.g. shampoo, shower gel; air care products and cosmetics, e.g. deodorant, vanishing creme. This list of products is given by way of illustration and is not to be regarded as being in any way limiting.

The compounds of formula (I) may be synthesized by reaction of the appropriately substituted 1-ethoxyvinyl lithium derivative or a related organometallic species with the appropriately substituted trialkylhalosilane with subsequent hydrolysis of the resulting trialkyl(ethoxyvinyl)silane to afford the corresponding acetyltrialkylsilane. Grignard reaction of this acetylsilane with an alkyl lithium or an alkyl magnesium reagent then completes the synthesis of the silacarbinols of formula (I). The aforementioned substituted trialkylhalosilanes are either commercially available or can be prepared by reaction of an appropriately substituted dialkyldihalosilane, alkyltrihalosilane or tetrahalosilane with a suitable alkyl lithium or alkyl magnesium reagent. The aforementioned 1-ethoxyvinyl lithium derivatives are itself accessible by reaction of the appropriately substituted ethyl alk-1-en-1-yl ether with tert-butyl lithium.

The invention is now further described with reference to the following non-limiting examples. These examples are for the purpose of illustration only and it is understood that variations and modifications can be made by one skilled in the art.

EXAMPLE 1

Dicyclopropyl(1-hydroxy-1-methylethyl)methylsilane

Within a period of 60 min., a solution of bromocyclopropane (20.0 g, 165 mmol) in $Et_2O$ (80 ml) was added dropwise with stirring at 0° C. under an atmosphere of argon to a suspension of lithium (2.30 g, 331 mmol) in $Et_2O$ (160 ml). After stirring for 60 min. at room temp, the solution was added at 0° C. during 30 min. dropwise to a solution of trichloromethylsilane (12.3 g, 72.4 mmol) in $Et_2O$ (80 ml). After 24 h of stirring at room temp., the suspension was filtered under an atmosphere of argon, and the filtrate was concentrated under reduced pressure. The resulting residue was distilled to provide at 68° C./21 mbar 7.90 g (60%) of chloro(dicyclopropyl)methylsilane.

Representative procedure for the preparation of acetylsilanes from monochlorosilanes: Under an atmosphere of argon, a 1.6 M solution of tert-butyl lithium in pentane (3.88 ml, 6.21 mmol) was added during 30 min. dropwise with stirring at −78° C. to a solution of ethyl vinyl ether (500 mg, 6.93 mmol) in THF (30 ml). The reaction mixture was then allowed to warm to 0° C. over a period of 3 h. At −50° C., chloro(dicyclopropyl)methyl-silane (1.00 g, 6.22 mmol) was then added in one single portion. After stirring for 16 h at room temp., the mixture was poured into water (30 ml) and was stirred for 10 min. The organic layer was separated, the aqueous one extracted with $Et_2O$ (2×30 ml). The combined organic solutions were dried ($Na_2SO_4$), and concentrated in a rotary evaporator to afford crude dicyclopropyl(1-ethoxyvinyl)methylsilane which was taken up in acetone/1N HCl (2:1, 12 ml). The reaction mixture was stirred for 45 min. at room temp. prior to the addition of water/$Et_2O$ (1:1, 30 ml). The organic layer was separated, and the aqueous one extracted with $Et_2O$ (2×15 ml). The combined ethereal extracts were dried ($Na_2SO_4$), and concentrated under reduced pressure. The resulting residue was purified by silica-gel chromatography (silica gel 40-63 μm, hexane/EtOAc, 9:1), and the relevant fractions were combined (GC) to provide 452 mg (43% over 2 steps) of acetyl(dicyclopropyl)methylsilane.

Representative procedure for the preparation of (1-hydroxy-1methylethyl)silanes from acetylsilanes: At 0° C. under argon atmosphere, a 1.6 M solution of methyl lithium in $Et_2O$ (15.1 ml, 24.2 mmol) was added during 10 min. dropwise with stirring to a solution of acetyl(dicyclopropyl)methylsilane (610 mg, 3.62 mmol) in THF (15 ml). After 24 h of stirring at room temp., the mixture was poured carefully into water (50 ml), and the product was extracted with $Et_2O$ (2×50 ml). The combined organic extracts were dried ($Na_2SO_4$), and concentrated in a rotary evaporator. The resulting residue was purified by silica-gel flash chromatography (silica gel 15-40 μm, hexane/EtOAc, 9:1), and the relevant fractions were combined (GC) to furnish 290 mg (44%) of the odoriferous title compound.

$^1$H-NMR (500.1 MHz, $CDCl_3$): δ=−0.48 (tt, 2H, J=10.0 Hz, J=7.0 Hz, $((CH_2)_2CH)_2Si)$, −0.31 (s, 3H, $SiCH_3$), 0.24-0.29 (m, 4H, $((CH_aH_bCH_cH_d)CH)_2Si)$, 0.52-0.59 (m, 4H, $((CH_aH_bCH_cH_d)CH)_2Si)$, 1.15 (s, 1H, SiCOH), 1.29 (s, 6H, $COH(CH_3)_2$). —$^{13}$C-NMR (125.8 MHz, $CDCl_3$): δ=−12.0 ($SiCH_3$), −9.8 (2C, $((CH_2)_2CH)_2Si)$, 0.3 (2C, $((CH_2)_a(CH_2)_bCH)_2Si)$, 0.7 (2C, $((CH_2)_a(CH_2)_bCH)_2Si)$, 27.8 (2C, SiCOH $(CH_3)_2$), 65.4 (SiCOH). —$^{29}$Si-NMR (99.4 MHz, $CDCl_3$): δ=6.53. —GC/EI-MS (pos.): m/z (%) 184 (1) [M$^+$], 169 (20) [M$^+$-$CH_3$]97 (100). —$C_{11}H_{20}OSi$ (184.4): calcd. C, 65.15; H, 10.93. found C, 64.89; H, 11.17.

Odour description: typical, very natural patchouli odour of agrestic and woody tonality with more pronounced borneol-like aspects upon dry down.

EXAMPLE 2

Tricyclopropyl(1-hydroxy-1-methylethyl)silane

At 0° C. under an atmosphere of argon, granular lithium (1.30 g, 187 mmol) was suspended in $Et_2O$ (60 ml), and a solution of bromocyclopropane (10.7 g, 88.5 mmol) in $Et_2O$ (60 ml) was added during 30 min. dropwise. After stirring 30 min. at 0° C., the resulting solution was added during 60 min. dropwise at this temp. to a solution of tetrachlorosilane (5.00 g, 27.0 mmol) in $Et_2O$ (120 ml), and stirring was continued for 7 h at room temp. In a separate vessel under an atmosphere of argon, a 1.6 M solution of tert-butyl lithium in pentane (18.4 ml, 29.4 mmol) was added during 30 min. dropwise with stirring at −78° C. to a solution of ethyl vinyl ether (2.12 g, 29.4 mmol) in THF (22 ml). This reaction mixture was then allowed to warm to 0° C. within 3 h, prior to being cooled to −50° C. and added dropwise with stirring during 10 min. at −50° C. to the first reaction mixture. After stirring for 16 h at room temp., the mixture was poured into water (200 ml), and stirring was continued for 10 min. The organic layer was separated, and the aqueous one extracted with $Et_2O$ (2×75 ml). The combined organic solutions were dried ($Na_2SO_4$), and concentrated in a rotary evaporator to afford crude tricyclopropyl(1-ethoxyvinyl)silane, which was taken up in acetone/1 N HCl (2:1, 72 ml). The reaction mixture was stirred for 45 min. prior to the addition of water/$Et_2O$ (1:1, 100 ml). The organic layer was separated, and the aqueous one extracted with $Et_2O$ (2×50 ml). The combined ethereal extracts were dried ($Na_2SO_4$) and concentrated under reduced pressure. Silica-gel chromatography (silica gel 40-63 μm, hexane/EtOAc, 9:1, relevant fractions were determined by GC) of the resulting residue provided 2.58 g (49% over 2 steps) of acetyl(tricyclopropyl)silane.

Under an atmosphere of argon, a 1.6 M solution of methyl lithium in $Et_2O$ (20.0 ml, 32.0 mmol) was added during 10 min. dropwise with stirring at 0° C. to a solution of acetyl (triicyclopropyl)silane (800 mg, 4.12 mmol) in THF (20 ml). After 24 h of stirring at room temp., the mixture was poured with caution into water (50 ml), and the product was extracted with $Et_2O$ (2×50 ml). The combined organic extracts were dried ($Na_2SO_4$), and concentrated in a rotary evaporator. Silica-gel flash chromatography (silica gel 15-40 μm, hexane/ EtOAc, 9:1, relevant fractions were determined by GC) of the resulting residue provided 492 mg (57%) of the odoriferous title compound.

$^1$H-NMR (500.1 MHz, $CDCl_3$): δ=−0.68 ($δ_x$, 3H, (($CH_2$)$_2$CH)$_3$Si), 0.39 ($δ_{AA'}$, 6H, (($CH_aCH_b$)$_2$CH)$_3$Si) and 0.52 ($δ_{MM'}$, 6H, (($CH_aH_b$)$_2$CH)$_3$Si, AA'MM'X-System, $^3J_{AA'}$=$^3J_{A'A}$=8.5 Hz, $^3J_{A'M'}$=5.0 Hz, $^2J_{AM}$=$^2J_{A'M'}$=−3.5 Hz, $^3J_{AX}$=$^3J_{A'X}$7.0 Hz, $^3J_{MX}$=$^3J_{M'X}$=10.0 Hz, $^3J_{MM'}$=$^3J_{M'M}$=8.0 Hz), 1.28 (s, 1H, SiCOH), 1.34 (s, 6H, SiCOH($CH_3$)$_2$). —$^{13}$C-NMR (125.8 MHz, $CDCl_3$): δ=−12.2 (3C, (($CH_2$)$_2$CH)$_3$Si), 0.24 (6C, (($CH_2$)$_2$CH)$_3$Si), 28.0 (2C, SiCOH($CH_3$)$_2$), 66.2 (SiCOH). —$^{29}$Si-NMR (99.4 MHz, $CDCl_3$): δ=4.45. —GC/EI-MS (pos.): m/z (%) 195 (2) [M$^+$-$CH_3$], 151 (70) [M$^+$-COH($CH_3$)$_2$], 95 (100). $C_{12}H_{22}OSi$ (210.4): calcd. C, 68.51; H, 10.54. found C, 68.15; H, 10.75.

Odour description: very powerful and natural woody-resinous patchouli odor with earthy and caryophyllene-like aspects and some reminiscence to Cashmeran (1,1,2,3,3-pentamethyl-2,3,6,7-tetrahydro-1H-inden-4(5H)-one) as well as Verdol (2-tert-butylcyclohexanol).

EXAMPLE 3

Dicyclopropyl(ethyl)(1-hydroxy-1-methylethyl)silane

Following the procedure for the preparation of dicyclopropyl(1-hydroxy-1-methylethyl)methylsilane (see Example 1), dicyclopropyl(ethyl)(1-hydroxy-1-methylethyl)silane was prepared from the precursors chloro(dicyclopropyl)ethylsilane and acetyl(dicyclopropyl)ethylsilane. Reaction of trichloro(ethyl)silane (10.2 g, 62.4 mmol) with cyclopropyl lithium (prepared from bromocyclopropane (15.2 g, 126 mmol) and Li (1.80 g, 259 mmol) in $Et_2O$ (80 ml)) followed by distillation (79° C., 20 mbar) afforded 5.43 g (50%) of dicyclopropyl(ethyl)chlorosilane. Reaction of dicyclopropyl (ethyl)chlorosilane (5.00 g, 28.6 mmol) with ethoxyvinyl lithium (prepared from ethyl vinyl ether (2.52 g, 35.0 mmol) and tert-butyl lithium (1.9 M in pentane, 16.5 ml, 31.4 mmol) in THF (45 ml)) followed by hydrolysis with acetone/1 N HCl (2:1, 64 ml) and purification by silica-gel chromatography (silica gel 40-63 μm, hexane/EtOAc, 9:1) afforded 2.00 g (38% over 2 steps) of acetyl(dicyclopropyl)ethylsilane, of which 1.10 g (6.03 mmol) was reacted with methyl lithium (1.6 M in $Et_2O$, 33.9 ml, 54.2 mmol) to provide after purification by silica-gel flash chromatography (silica gel 15-40 μm, hexane/EtOAc, 9:1) 720 mg (60%) of the odoriferous title compound.

$^1$H-NMR (500.1 MHz, $CDCl_3$): δ=−0.52 (tt, 2H, J=10.0 Hz, J=7.0 Hz, (($CH_2$)$_2$CH)$_2$Si), 0.31-0.35 (m, 4H, (($CH_aH_b$-$CH_d$)CH)$_2$Si), 0.38 (q, 2H, J=8.0 Hz, $SiCH_2CH_3$), 0.53-0.59 (m, 4H, (($CH_aH_bCH_d$)CH)$_2$Si), 1.00 (t, 3H, J=8.0 Hz, $SiCH_2CH_3$), 1.15 (s, 1H, SiCOH), 1.29 (s, 6H, SiCOH($CH_3$)$_2$). —$^{13}$C-NMR (125.8 MHz, $CDCl_3$): δ=−10.8 (2C, (($CH_2$)$_2$CH)$_2$Si), −0.3 ($SiCH_2CH_3$), 0.3/0.8 (4C, (($CH_2$)$_2$CH)$_2$ Si), 7.9 ($SiCH_2CH_3$), 28.2 (2C, SiCOH($CH_3$)$_2$), 66.0 (SiCOH). —$^{29}$Si-NMR (99.4 MHz, $CDCl_3$): δ=4.23. —GC/EI-MS (pos.): m/z (%) 198 (<1) [M$^{30}$], 169 (40) [M$^+$-$CH_2CH_3$], 83 (100). $C_{11}H_{22}OSi$ (198.4): calcd. C, 66.60; H, 11.18. found C, 66.42; H, 11.12.

Odour description: Patchouli-type odor with earthy aspects and nuances of Verdol (2-tert-butylcyclohexanol) and borneol.

EXAMPLE 4

Dicyclopropyl(1-hydroxy-1-methylethyl)isopropylsilane

Under an atmosphere of argon, a 0.7 M solution of isopropyl lithium in pentane (22.3 ml, 15.6 mmol) was added in one portion with stirring at −15° C. to a solution of tetrachlorosilane (3.00 g, 17.7 mmol) in pentane (60 ml). The reaction mixture was then allowed to warm to room temp. over a period of 2 h, and stirring was continued for 20 h at room temp. In a different vessel, also under an atmosphere of argon, granular lithium (620 mg, 89.3 mmol) was suspended in $Et_2O$ (60 ml), and a solution of bromocyclopropane (4.27 g, 35.3 mmol) in $Et_2O$ (20 ml) was added during 45 min. dropwise at 0° C. After stirring for 10 min. at room temp., the resulting solution was added during 30 min. dropwise at 0° C. to the above mentioned reaction mixture, and the resulting suspension was stirred for 20 h at room temp. At −78° C. under argon atmosphere, a 1.6 M solution of tert-butyl lithium in pentane (16.8 ml, 26.9 mmol) was added during 30 min. dropwise with stirring to a solution of ethyl vinyl ether (2.25 g, 31.2 mmol) in THF (20 ml). This reaction mixture was then allowed to warm to 0° C. over a period of 3 h, prior to the dropwise addition to the first reaction mixture at −50° C. After stirring at −40° C. for 20 min and at room temp. for 20 h, the reaction mixture was poured into water (200 ml), and was stirred for 10 min. The organic layer was separated, and the aqueous one extracted with $Et_2O$ (2×100 ml). The combined organic solutions were dried ($Na_2SO_4$) and concentrated in a rotary evaporator. The resulting residue was taken up in acetone/1 N HCl (2:1, 12 ml). The mixture was stirred for 45 min., followed by addition of water/$Et_2O$ (1:1, 80 ml). The organic layer was separated, and the aqueous one extracted with $Et_2O$ (2×40 ml). The combined ethereal extracts were dried ($Na_2SO_4$), and concentrated under reduced pressure. Repeated silica-gel chromatography (silica gel 40-63 μm, hexane/EtOAc, 95:5, relevant fractions were determined by GC) of the resulting residue provided 320 mg (9% over 3 steps) of acetyl(dicyclopropyl)isopropylsilane, 310 mg (1.58 mmol) of which were reacted with methyl lithium (1.6 ha in $Et_2O$, 8.00 ml, 12.8 mmol) following the general procedure for the preparation of (1-hydroxy-1-methylethyl)silanes (see Example 1) to provide after purification by silica-gel flash chromatography (silica gel 15-40 μm, hexane/EtOAc, 9:1, relevant fractions were determined by GC) 170 mg (51%) of the odoriferous title compound.

$^1$H-NMR (500.1 MHz, $CDCl_3$): δ=−0.56 (tt, 2H, J=10.0 Hz, J=7.0 Hz, (($CH_2$)$_2$CH)$_2$Si), 0.36-0.45 (m, 4H, (($CH_aH_b$-$CH_cH_d$)CHSi), 0.54-0.60 (m, 4H, (($CH_aH_bCH_cH_d$)CHSi), 0.87-0.96 (m, 1H, ($CH_3$)$_2$CHSi), 1.08 (d, 6H, J=7.0 Hz, ($CH_3$)$_2$CHSi), 1.17 (s, 1H, SiCOH), 1.30 (s, 6H, SiCOH($CH_3$)$_2$). —$^{13}$C-NMR (125.8 MHz, $CDCl_3$): δ=10.7 (2C, (($CH_2$)$_2$CH)$_2$Si), 0.8/1.0 (4C, (($CH_2$)$_2$CH)$_2$Si), 11.5 (($CH_3$)$_2$CHSi), 19.1 (2C, ($CH_3$)$_2$CHSi), 28.9 (2C, SiCOH($CH_3$)$_2$), 66.6 (SiCOH). —$^{29}$Si-NMR (99.4 MHz, $CDCl_3$): δ=1.33. —GC/EI-MS (pos.): m/z (%) 169 (35) [M$^+$-CH($CH_3$)$_2$], 153 (40) [M$^+$-COH($CH_3$)$_2$], 43 (100). $C_{12}H_{24}OSi$ (212.4): calcd. C, 67.86; H, 11.39. found C, 67.71; H, 11.32.

Odour description: Woody, patchouli-like note of slightly waxy connotation.

EXAMPLE 5 rac-(±)-Dicyclopropyl(1-hydroxy-1-methylpropyl)methylsilane

Acetyl(dicyclopropyl)methylsilane was prepared according to the procedure in Example 1. Under an atmosphere of argon, a 1.7 M solution of ethyl lithium in n-Bu$_2$O (22.5 ml, 38.3 mmol) was added during 10 min. dropwise with stirring at 0° C. to a solution of acetyl(dicyclopropyl)methylsilane (1.50 g, 8.91 mmol) in THF (20 ml). After 24 h of stirring at room temp., the mixture was poured with caution into water (50 ml), and the product was extracted with Et$_2$O (2×45 ml). The combined organic extracts were dried (Na$_2$SO$_4$), and concentrated in a rotary evaporator. Silica-gel flash chromatography (silica gel 15-40 μm, hexane/EtOAc, 9:1, relevant fractions were determined by GC) of the resulting residue provided 420 mg (24%) of the odoriferous title compound.

$^1$H-NMR (500.1 MHz, CDCl$_3$): δ=–0.47 (m, 2H, ((CH$_2$)$_2$CH)$_2$Si), –0.31 (s, 3H, SiCH$_3$), 0.24-0.29 (m, 4H, ((CH$_a$H$_b$CH$_c$H$_d$)CH)$_2$Si), 0.50-0.61 (m, 4H, ((CH$_a$H$_b$CH$_c$H$_d$)CH)$_2$Si), 0.94 (δ$_x$, 3H, CH$_3$CH$_2$), 1.63 (δ$_A$, 1H, CH$_3$CH$_A$H$_B$) and 1.71 (δ$_B$, 1H, CH$_3$CH$_A$H$_B$, ABX$_3$-System, $^2$J$_{AB}$=14 Hz, $^3$J$_{AX}$=$^3$J$_{BX}$=7.5 Hz), 1.15 (s, 1H, SiCOH), 1.25 (s, 3H, SiCOHCH$_3$). —$^{13}$C-NMR (125.8 MHz, CDCl$_3$): δ=–11.6 (SiCH$_3$), –9.41-9.3 (2C, (CH$_2$)$_2$CH)$_2$Si), 0.4/05/0.9/0.9 (4C, ((CH$_2$)$_2$CH)$_2$Si), 7.24 (CH$_3$CH$_2$), 23.8 (SiCOHCH$_3$), 32.6 (CH$_3$CH$_2$), 67.7 (SiCOH). —$^{29}$Si-NMR (99.4 MHz, CDCl$_3$): δ=6.64.—GC/EI-MS (pos.): m/z (%) 198 (<1) [M$^+$], 183 (10) [M$^+$-CH$_3$], 169 (20) [M$^+$-CH$_2$CH$_3$], 97 (100). C$_{11}$H$_{22}$OSi (198.4): calcd. C, 66.60; H, 11.18. found C, 66.34; H, 11.36.

Odour description: earthy, rooty, musty humus-type odor with patchouli aspects and nuances of Verdol (2-tert-butylcyclohexanol) and borneol.

EXAMPLE 6

Dicyclopropyl(1-ethyl-1-hydroxypropyl)methylsilane

Under an atmosphere of argon, a 1.9 M solution of tert-butyl lithium in pentane (10.0 ml, 19.0 mmol) was added in one portion with stirring at –78° C. to a solution of (E/Z)-1-ethoxyprop-1-ene (1.61 g, 18.7 mmol) in pentane (20 ml). The reaction mixture was then allowed to warm to 0° C. within 30 min. Subsequently, TMEDA (5.39 g, 46.4 mmol) was added, and the reaction mixture was allowed to warm to room temp. After stirring for 1 h at room temp., the mixture was cooled to –78° C. and chloro(dicyclopropyl)-methylsilane (3.00 g, 18.7 mmol, prepared according to Example 1) was added dropwise over a period of 30 min. After a further 16 h stirring at room temp., the mixture was poured into water (50 ml). After 10 min. of stirring, the organic layer was separated, and the aqueous one extracted with Et$_2$O (2×50 ml). The combined organic extracts were dried (Na$_2$SO$_4$), and concentrated under reduced pressure to afford crude dicyclopropyl(1-ethoxypropionyl)methylsilane, which was taken up in acetone/1 N HCl (2:1, 48 ml). The reaction mixture was stirred for 45 min. at room temp. followed by the addition of water/Et$_2$O (1:1, 100 ml). The organic layer was separated, and the aqueous one extracted with Et$_2$O (2×30 ml). The combined ethereal extracts were dried (Na$_2$SO$_4$) and concentrated under reduced pressure. Silica-gel chromatography (silica gel 40-63 μm, hexane/EtOAc, 9:1, relevant fractions were determined by GC) followed by bulb-to-bulb distillation (0.08 mbar, 40° C.) of the resulting residue provided 437 mg (13% over 2 steps) of dicyclopropyl(methyl)propionylsilane. Following the procedure for the preparation of dicyclopropyl (1-hydroxy-1-methylpropyl)methylsilane (see Example 5), dicyclopropyl(methyl)propionylsilane (470 mg, 2.58 mmol) was then reacted with ethyl lithium (1.7 M in n-Bu$_2$O, 12.1 ml, 20.6 mmol) to provide after purification by silica-gel flash chromatography (silica gel 40-63 μm, hexane/EtOAc, 9:1) 360 mg (66%) of the odoriferous title compound.

$^1$H-NMR (500.1 MHz, CDCl$_3$): δ=–0.46 (ft, 2H, J=10.0 Hz, J=7.0 Hz, ((CH$_2$)$_2$CH)$_2$Si), –0.30 (s, 3H, SiCH$_3$), 0.24-0.30 (m, 4H, ((CH$_a$H$_b$CH$_c$H$_d$)CH)$_2$Si), 0.50-0.61 (m, 4H, ((CH$_a$H$_b$CH$_c$H$_d$)CH)$_2$Si), 0.91 (δ$_{x3}$, 6H, CH$_2$CH$_3$), 1.67 (δ$_A$, 2H, CH$_3$CH$_A$H$_B$) and 1.72 (δ$_B$, 2H, CH$_3$CH$_A$H$_B$, ABX$_3$-System, $^2$J$_{AB}$=14 Hz, $^3$J$_{AX}$=$^3$J$_{BX}$=7.5 Hz), 1.17 (SiCOH). —$^{13}$C-NMR (125.8 MHz, CDCl$_3$): δ=–11.0 (SiCH$_3$), –8.7 (2C, ((CH$_2$)$_2$CH)$_2$Si), 0.7/1.2 (4C, ((CH$_2$)$_2$CH)$_2$Si), 7.8 (2C, SiCOH(CH$_2$CH$_3$)$_2$), 29.2 (2C, SiCOH(CH$_2$CH$_3$)$_2$), 70.7 (SiCOH). —$^{29}$Si-NMR (99.4 MHz, CDCl$_3$): δ=6.90. —GC/EI-MS (pos.): m/z (%) 197 (2) [M$^+$-CH$_3$], 183 (10) [M$^+$-CH$_2$CH$_3$], 125 (50) [M$^+$-C(OH)(CH$_2$CH$_3$)$_2$], 43 (100). C$_{12}$H$_{24}$OSi (212.4): calcd. C, 67.86; H, 11.39. found C, 67.76; H, 11.49.

Odour description: borneol-like, earthy odour with some woody, patchouli-type aspects on top of a creamy fond.

EXAMPLE 7

(1-Hydroxy-1-methylethyl)(diisopropyl)methylsilane

Under an atmosphere of argon, a 1.9 M solution of tert-butyl lithium in pentane (14.2 ml, 27.0 mmol) was added at –78° C. during 20 min. dropwise with stirring to a solution of ethyl vinyl ether (2.00 g, 27.7 mmol) in THF (30 ml). The reaction mixture was then allowed to warm to 0° C. within 3 h. Subsequently, it was cooled to –50° C., and then added to a solution of dichloro(diisopropyl)silane (5.00 g, 27.0 mmol) at –50° C. during a period of 10 min. After stirring for 16 h at room temp., a 1.6 M solution of methyl lithium in Et$_2$O (33.8 ml, 54.1 mmol) was added dropwise with stirring within 10 min. at 0° C. After further 16 h of stirring at room temp., the mixture was poured into water (100 ml) with caution. After stirring for 10 min., the organic layer was separated, and the aqueous one was extracted with Et$_2$O (2×100 ml). The combined organic solutions were dried (Na$_2$SO$_4$), and concentrated in a rotary evaporator. Following the general procedure for the preparation of acetylsilanes (see Example 1), the crude (1-ethoxyvinyl)(diisoproyl)methylsilane was then hydrolysed with acetone/1 N HCl (2:1, 24 ml) to afford after silica-gel chromatography (silica gel 40-63 μm, hexane/EtOAc, 95:5) 1.60 g (34% over 2 steps) of acetyl(diisopropyl)methylsilane, of which 1.50 g (8.70 mmol) reacted according to Example 1 with methyl lithium (1.6 M in Et$_2$O, 41.0 ml, 65.6 mmol) to provide after purification by silica-gel flash chromatography (silica gel 15-40 μm, hexane/EtOAc, 9:1) 870 mg (53%) of the odoriferous title compound.

$^1$H-NMR (500.1 MHz, CDCl$_3$): δ=–0.04 (s, 3H, SiCH$_3$), 0.95 (s, 1H, SiCOH), 1.05 (m, 14H, Si(CH(CH$_3$)$_2$), 1.25 (s, 6H, SiCOH(CH$_3$)$_2$). —$^{13}$C-NMR (125.8 MHz, CDCl$_3$): δ=–10.3 (SiCH$_3$), 11.3 (2C, Si(CH(CH$_3$)$_2$)$_2$), 18.9/19.1 (4C, SiCH(CH$_3$)$_2$), 29.5 (2C, SiCOH(CH$_3$)$_2$), 66.0 (SiCOH). —$^{29}$Si-NMR (99.4 MHz, CDCl$_3$): δ=6.64. —GC/EI-MS (pos.): m/z (%) 170 (10) [M$^+$-H$_2$O], 75 (100). C$_{10}$H$_{24}$OSi (188.4): calcd. C, 63.76; H, 12.84. found C, 63.76; H, 12.81.

Odour description: diffusive woody, patchouli odour of camphoraceous tonality with some earthy-mossy nuances.

EXAMPLE 8

Cyclopropyl(1-hydroxy-1-methylethyl)(diisopropyl)silane

According to the synthesis of 1-hydroxy-1-methylethyl (diisopropyl)methylsilane (Example 7), cyclopropyl(1-hydroxy-1-methylethyl)(diisopropyl)silane was prepared from dichloro(diisopropyl)silane (5.00 g, 27.0 mmol), ethoxyvinyl lithium (prepared from ethyl vinyl ether (2.17 g, 30.1 mmol) and tert-butyl lithium (1.9 M in pentane, 14.2 ml, 27.0 mmol) in THF (40 ml)) and cyclopropyl lithium (prepared according to Example 1 from bromocyclopropane (3.59 g, 29.7 mmol) and lithium (412 mg, 59.4 mmol) in Et$_2$O). The crude cyclopropyl(1-ethoxyvinyl)(diisopropyl)silane was hydrolysed with acetone/1 N HCl (2:1, 72 ml), and purified by silica-gel flash chromatography (silica gel 40-63 μm, hexane/EtOAc, 9:1) to afford 2.11 g (39%) acetyl(cyclopropyl)(diisopropyl)silane. Reaction of acetyl(cyclopropyl)(diisopropyl)silane (1.00 g, 5.04 mmol) with methyl lithium (1.6 M in Et$_2$O, 25.2 ml, 40.3 mmol) afforded after purification by silica-gel chromatography (silica gel 15-40 μm, hexane/EtOAc, 9:1) 590 mg (55%) of the odoriferous title compound.

$^1$H-NMR (500.1 MHz, CDCl$_3$): δ=−0.41 ($δ_X$, 1H, ((CH$_2$)$_2$CH)$_3$Si), 0.46 ($δ_{AA'}$, 2H, ((CH$_a$H$_b$)$_2$CH)$_3$Si) and 0.63 ($δ_{MM'}$, 2H, ((CH$_a$H$_b$)$_2$CH)$_3$Si, AA'MM'X-System, $^3J_{AA'}=^3J_{A'A}$=8.5 Hz, $^3J_{AM'}=^3J_{A'M}$=5.0 Hz, $^2J_{AM}=^2J_{A'M'}$=−3.5 Hz, $^3J_{AX}=^3J_{A'X}$=7.0 Hz, $^3J_{MX}=^3J_{M'X}$=10.0 Hz, $^3J_{MM'}=^3J_{M'M}$=8.5 Hz), 1.02-1.12 (m, 15H, ((CH$_3$)$_2$CH)$_2$Si, SiCOH), 1.30 (s, 6H, SiCOH(CH$_3$)$_2$). —$^{13}$C-NMR (125.8 MHz, CDCl$_3$): δ=−9.1 ((CH$_2$)$_2$CHSi), 1.7 (2C, (CH$_2$)$_2$CHSi), 11.4 (2C, ((CH$_3$)$_2$CH)$_2$Si), 19.2/19.2 (4C, ((CH$_3$)$_2$CH)$_2$Si), 29.9 (2C, SiCOH(CH$_3$)$_2$), 67.0 (SiCOH). —$^{29}$Si-NMR (99.4 MHz, CDCl$_3$): δ=0.92. —GC/EI-MS (pos.): m/z (%) 214 (<1) [M$^+$], 199 (3) [M$^-$-CH$_3$], 171 (15) [M$^+$-(CH$_3$)$_2$CH], 85 (100). C$_{12}$H$_{26}$OSi (214.4): calcd. C, 67.22; H, 12.22. found C, 67.12; H, 12.24.

Odour description: green-earthy, rooty humus-like odour reminiscent of wet soil with some aspects of patchouli oil and beetroot.

EXAMPLE 9

(1-Hydroxy-1-methylethyl)triisopropylsilane

Following the procedure for the preparation of acetylsilanes (see Example 1), (1-hydroxy-1-methylethyl)triisopropylsilane was prepared from chlorotriisopropylsilane (10.0 g, 51.9 mmol) and ethoxyvinyl lithium (prepared from ethyl vinyl ether (4.05 g, 56.2 mmol) and tert-butyl lithium (1.9 M in pentane, 27.3 ml, 51.9 mmol) in THF (60 ml)). The crude product was hydrolysed with acetone/1 N HCl (2:1, 90 ml), and purified by silica-gel flash chromatography (silica gel 40-63 μm, hexane/EtOAc, 95:5) to afford 4.45 g (43% over 2 steps) of acetyltriisopropylsilane, of which 4.40 g (22.1 mmol) was reacted with methyl lithium (1.6 M in Et$_2$O, 100 ml, 160 mmol) to furnish after purification by silica-gel chromatography (silica gel 15-40 μm, hexane/EtOAc, 9:1) 1.11 g (23%) of the odoriferous title compound.

$^1$H-NMR (500.1 MHz, CDCl$_3$): δ=0.96 (s, 1H, SiCOH), 1.12-1.13 (m, 18H, ((CH$_3$)$_2$CH)$_3$Si), 1.18-1.27 ((m, 3H, ((CH$_3$)$_2$CH)$_3$Si), 1.31 (s, 6H, (2C, SiCOH(CH$_3$)$_2$). —$^{13}$C-NMR (125.8 MHz, CDCl$_3$): δ=10.9 (3C, ((CH$_3$)$_2$CH)$_3$Si), 19.4 (6C, ((CH$_3$)$_2$CH)$_3$Si), 31.0 (2C, SiCOH(CH$_3$)$_2$), 67.2 (SiCOH). —$^{29}$Si-NMR (99.4 MHz, CDCl$_3$): δ=2.53. —GC/EI-MS (pos.): m/z (%) 198 (5) [M$^+$-H$_2$O], 59 (100). C$_{12}$H$_{28}$OSi (216.4): calcd. C, 66.59; H, 13.04. found C, 66.38; H, 13.20.

Odour description: borneol-like piney odour with earthy aspects recalling wet soil, as well as a patchouli character and green, terpenic aspects.

EXAMPLE 10 rac-(±)-(1-Hydroxy-1-methylethyl)(isobutyl)(isopropyl(methyl)silane

Following the procedure for the preparation of diisopropyl (1-hydroxy-1-methylethyl)methylsilane, rac-(±)-(1-hydroxy-1-methylethyl)isobutylisopropyl-methylsilane was prepared from dichloro(isobutyl)methylsilane (5.00 g, 29.2 mmol), isopropyl lithium (0.7 M in pentane, 41.7 ml, 29.2 mmol) and ethoxyvinyl lithium (prepared from ethyl vinyl ether (2.34 g, 32.5 mmol) and tert-butyl lithium (1.9 M in pentane, 15.4 ml, 29.3 mmol) in THF (120 ml)). The crude product was hydrolysed with acetone/1 N HCl (2:1, 32 ml). Purification by silica-gel chromatography (50×3 cm diameter, silica gel 40-63 μm, 180 g, hexane/EtOAc, 9:1) afforded 1.61 g (30% over 2 steps) of rac-(±)-acetyl(isobutypisopropyl (methyl)silane, of which 1.09 g (5.85 mmol) was reacted with methyl lithium (1.6 M in Et$_2$O, 20.0 ml, 32.0 mmol) to provide after purification by silica-gel flash chromatography (50×1.5 cm diameter, silica gel 40-63 μm, 45 g, hexane/EtOAc, 9:1) 550 mg (46%) of the odoriferous title compound.

$^1$H-NMR (500.1 MHz, CDCl$_3$): δ=0.03 (s, 3H, SiCH$_3$), 0.56 ($δ_A$, 1H, CH$_A$H$_B$CH(CH$_3$)$_2$), 0.62 ($δ_B$, 1H, CH$_A$H$_B$CH(CH$_3$)$_2$), 0.94 ($δ_M$, 6H, CH$_A$H$_B$CH(CH$_3$)$_2$) und 1.81 ($δ_X$, 1H, CH$_A$H$_B$CH(CH$_3$)$_2$, ABM$_6$X-System, $^2J_{AB}$=15.0 Hz, $^3J_{AX}$=6.5 Hz, $^3J_{BX}$=7.0 Hz, $^3J_{MX}$=6.5 Hz), 0.86 (s, 1H, SiCOH), 0.95-1.02 (m, 1H, CH(CH$_3$)$_2$), 1.03 (d, 6H, CH(CH$_3$)$_2$), 1.21/1.21 (s, 6H, COH(CH$_3$)$_2$). —$^{13}$C-NMR (125.8 MHz, CDCl$_3$): δ=−8.1 (SiCH$_3$), 12.3 (CH$_3$)$_2$CHSi), 18.6/18.8 (2C, (CH$_3$)$_2$CHSi), 20.4 ((CH$_3$)$_2$CHCH$_2$Si), 24.8 ((CH$_3$)$_2$CHCH$_2$Si), 26.5/26.8 (2C, (CH$_3$)$_2$CHCH$_2$Si), 28.7/28.7 (2C, SiCOH(CH$_3$)$_2$), 65.4 (SiCOH). —$^{29}$Si-NMR (99.4 MHz, CDCl$_3$): δ=5.15. —GC/EI-MS (pos.): m/z (%) 159 (10) [M$^+$-(CH$_3$)$_2$CH], 59 (100). C$_{11}$H$_{26}$OSi (202.4): calcd. C, 65.27; H, 12.95. found C, 65.08; H, 12.99.

Odour description: agrestic odour with some reminiscence to borneol and camphor and slight patchouli aspects.

EXAMPLE 11

Di-tert-butyl(1-hydroxy-1-methylethyl)methylsilane

Di-tert-butyldifluorosilane was prepared according to the procedure of B. Rempfer et al., *J. Am. Chem. Soc.* 1986, 108, 3893-3897. Following the general procedure of Example 7, di-tert-butyl(1-hydroxy-1-methylethyl)methylsilane was prepared from di-tert-butyldifluorosilane (11.8 g, 65.4 mmol), ethoxyvinyl lithium (prepared from ethyl vinyl ether (4.68 g, 64.9 mmol) and tert-butyl lithium (1.6 M in pentane, 40.6 ml, 65.0 mmol)) in THF (100 ml)) and methyl lithium (1.6 M in Et$_2$O, 280 ml, 448 mmol). The crude product was distilled twice to furnish at 57° C./1.7 mbar 2.10 g (14%) of di-tert-butyl(1-ethoxyvinyl)methylsilane, of which 2.00 g (8.76 mmol) were hydrolysed with acetone/1 N HCl (2:1, 10 ml). Purification by silica-gel chromatography (silica-gel 35-70 μm, hexane/EtOAc, 9:1) followed by bulb-to-bulb distillation (120° C., 80 mbar) afforded 0.93 g (53%) of acetyl (di-tert-butyl)methylsilane (m.p. 35° C.), of which 0.90 g (4.49 mmol) was reacted with methyl lithium (1.6 M in Et$_2$O, 60.0 ml, 96.0 mmol) according to Example 1 to furnish after purification by repeated silica-gel flash chromatography (silica-gel 15-40 μm, hexane/EtOAc, 9:1) 204 mg (21%) of the odoriferous title compound (m.p. 122-123° C.).

$^1$H-NMR (500.1 MHz, CDCl$_3$): δ=0.01 (s, 3H, SiCH$_3$), 0.98 (s, 1H, SiCOH), 1.06 (s, 18 H, Si(C(CH$_3$)$_3$)$_2$), 1.35 (s, 6H, SiCOH(CH$_3$)$_2$). —$^{13}$C-NMR (125.8 MHz, CDCl$_3$): δ=−9.2 (SiCH$_3$), 20.3 (2C, Si(C(CH$_3$)$_3$)$_2$), 29.7 (6C, Si(C(CH$_3$)$_3$)$_2$), 31.0 (2C, SiCOH(CH$_3$)$_2$), 67.5 (SiCOH). —$^{29}$Si-NMR (99.4 MHz, CDCl$_3$): δ=7.51. —GC/EI-MS (pos.): m/z (%) 198 (2) [M$^+$-H$_2$O], 159 (25) [M$^+$-(C(CH$_3$)$_3$)], 73 (100), C$_{12}$H$_{28}$OSi (216.4): calcd. C, 66.59; H, 13.04. found C, 66.33; H, 13.05.

Odour description: green, woody-mossy odour reminiscent of tobacco, and slight patchouli aspects.

EXAMPLE 12 tert-Butyl(1-hydroxy-1-methylethyl)dimethylsilane

Following the general procedure for the preparation of acetylsilanes (see Example 1) tert-butyl(1-hydroxy-1-methylethyl)dimethylsilane was prepared from tert-butylchlorodimethylsilane (5.00 g, 33.2 mmol) and ethoxyvinyl lithium (prepared from ethyl vinyl ether (3.11 g, 43.1 mmol) and tert-butyl lithium (1.9 M in pentane, 22.7 ml, 43.1 mmol) in THF (50 ml)). The crude material was hydrolysed with acetone/1 N HCl (2:1, 60 ml), and purified by silica-gel chromatography (silica-gel 40-63 µm, hexane/EtOAc, 9:1) to afford 2.13 g (41% over 2 steps) of acetyl(tert-butyl)dimethylsilane, of which 1.44 g, (9.10 mmol) was reacted according to Example 1 with methyl lithium (1.6 M in Et$_2$O, 28.4 ml, 45.4 mmol) to provide after purification by silica-gel flash chromatography (silica-gel 15-40 µm, hexane/EtOAc, 9:1) 590 mg (37%) of the odoriferous title compound.

$^1$H-NMR (300.1 MHz, CDCl$_3$): δ=0.00 (s, 6H, Si(CH$_3$)$_2$), 0.96 (s, 9H, SiC(CH$_3$)$_3$), 1.25 (s, 6H, SiCOH(CH$_3$)$_2$), 0.91 (s, 1H, SiCOH). —$^{13}$C-NMR (75.5 MHz, CDCl$_3$): δ=−7.7 (2C, Si(CH$_3$)$_2$), 17.7 (SiC(CH$_3$)$_3$), 27.7 (3C, SiC(CH$_3$)$_3$), 29.1 (2C, SiCOH(CH$_3$)$_2$), 65.7 (SiCOH). —$^{29}$Si-NMR (59.6 MHz, CDCl$_3$): δ=8.02. —GC/EI-MS (pos.): m/z (%) 159 (5) [M$^+$-CH$_3$], 73 (100). C$_9$H$_{22}$OSi (174.4): calcd. C, 62.00; H, 12.72.

Odour description: green, camphoraceous and borneol-like odour in the direction of patchouli oil with slightly earthy and medicinal aspects.

EXAMPLE 13

Woody-Sweet-Herbaceous Shower Gel Perfume

| Compound/Ingredient | Parts per Weight 1/100 |
|---|---|
| 1. 2-tert-Butyl-5-methyl-2-propyl-2,5-dihydrofuran (Cassyrane ™) | 3 |
| 2. 2-Cyclohexyl-1,6-heptadien-3-one (Pharaone ™) @ 10% solution in dipropylene glycol (DPG) | 3 |
| 3. 1-(3'-Cycloocten-1'-yl)ethanone (Tanaisone ™) | 4 |
| 4. 1-Cyclopropylmethyl-4-methoxybenzene (Toscanol ™) | 8 |
| 5. 1,1-Diethoxy-3,7-dimethyl-2,6-octadiene (Citrathal ™) | 2 |
| 6. 2-(3',5'-Dimethylhex-3'-en-2'-yloxy)-2-methylpropyl cyclopropanecarboxylate (Sylkolide ™) | 5 |
| 7. Ethyl linalool (3,7-dimethylnona-1,6-dien-3-ol) | 10 |
| 8. (3Z)-Hex-3-en-1-ol | 5 |
| 9. 1-Hydroxy-2-(1'-methyl-1'-hydroxyethyl)-5-methylcyclohexane (Geranodyle ™) | 15 |
| 10. Methyl 1,4-dimethylcyclohexylcarboxylate (Cyprisate ™) | 30 |
| 11. Methyl 2-(3'-oxo-2'-pentylcyclopentyl)acetate (Hedione ™) | 5 |
| 12. Pink pepper oil (*Schinus molle*) pure | 5 |
| 13. Dicyclopropyl(1-hydroxy-1-methylethyl)methylsilane | 5 |

This perfume oil, applied @ 0.2% in transparent shower gel, evokes the sweet herbaceous odour of a pygmy cedar (*Cedrus deodara*). At a dosage of only 5%, the dicyclopropyl (1-hydroxy-1-methylethyl)methylsilane reinforces the natural, resinous and fir-type aspects, while providing a pleasant natural patchouli character to the overall composition. Thereby, it enhances the freshness of the product, and the resulting crisp uplifting scent stresses a mild, protective functional effect of the shower gel.

EXAMPLE 14

Masculine Foupère Fine Fragrance with Dicyclopropyl(1-hydroxy-1-methylethyl)methylsilane Instead of Patchouli Oil

| Compound/Ingredient | Parts per Weight 1/800 |
|---|---|
| 1. Clary sage oil, France | 10 |
| 2. Dihydromyrcenol | 45 |
| 3. 1,4-Dioxacycloheptadecane-5,17-dione (Brassylate ™) | 80 |
| 4. 2-(2",4"-Dimethylcyclohex-3"-ene-1"-yl)-5-methyl-(1'-methylpropyl)-1,3-dioxane (Karanal ™) | 50 |
| 5. Dipropylene glycol (DPG) | 60 |
| 6. Eugenol | 15 |
| 7. Galbex ® 183 Base (Firmenich) @ 10% in DPG | 45 |
| 8. 4-(4'-Hydroxy-4'-methylpentyl)cyclohex-3-en-1-carboxaldehyde (Cyclohexal ™) | 55 |
| 9. 1-(4'-Hydroxyphenyl)butan-3-one (Raspberry Ketone) | 50 |
| 10. Lemon oil, Italy | 25 |
| 11. Linalool | 45 |
| 12. 6-Methoxy-2,6-dimethyloctanal (Calypsone ™) | 20 |
| 13. Methyl 2,4-dihydroxy-3,6-dimethylbenzoate (Evernyl ™) | 10 |
| 14. 4-Methyl-2-(2'-methylpropyl)tetrahydro-2H-pyran-4-ol (Florosa ™) | 150 |
| 15. Orange oil, Brazil | 10 |
| 16. (10E)-Oxacycloheptadec-10-en-2-one (Ambrettolide ™) | 40 |
| 17. 4-(5',5',6'-Trimethylbicyclo[2.2.1]hept-2'-yl)cyclohexan-1-ol (Sandela ™) @ 85% in isopropyl myristate | 65 |
| 18. Dicyclopropyl(1-hydroxy-1-methylethyl)methylsilane | 25 |

This masculine fougère fine fragrance composition, free from salicylates and patchouli oil, is build around the interplay of Karanal (2-(2",4"-dimethylcyclohex-3"-ene-1"-yl)-5-methyl-(1'-methylpropyl)-1,3-dioxane), raspberry ketone (1-(4'-hydroxyphenyl)butan-3-one) and the patchouli note of dicyclopropyl(1-hydroxy-1-methylethyl)methylsilane. This latter sila-substituted carbinol pushes at around 3% in particular the top notes of the composition, and enhances the fruity character of the raspberry ketone. Besides it blends very well with dihydromyrcenol, Ambrettolide™ ((10E)-oxacycloheptadec-10-en-2-one) and Calypsone (6-methoxy-2,6-dimethyloctanal), thereby leading to a fresher, more lively and lush overall composition.

EXAMPLE 15

Masculine Fougère Fine Fragrance with Tricyclopropyl-(1-hydroxy-1-methylethyl)silane Instead of Patchouli Oil

| Compound/Ingredient | Parts per Weight 1/800 |
|---|---|
| 1. Clary sage oil, France | 10 |
| 2. Dihydromyrcenol | 45 |
| 3. 1,4-Dioxacycloheptadecane-5,17-dione (Brassylate ™) | 80 |

-continued

| | Compound/Ingredient | Parts per Weight 1/800 |
|---|---|---|
| 4. | 2-(2",4"-Dimethylcyclohex-3"-ene-1"-yl)-5-methyl-(1'-methylpropyl)-1,3-dioxane (Karanal ™) | 50 |
| 5. | Dipropylene glycol (DPG) | 55 |
| 6. | Eugenol | 15 |
| 7. | Galbex ® 183 Base (Firmenich) @ 10% in DPG | 45 |
| 8. | 4-(4'-Hydroxy-4'-methylpentyl)cyclohex-3-en-1-carboxaldehyde (Cyclohexal ™) | 55 |
| 9. | 1-(4'-Hydroxyphenyl)butan-3-one (Raspberry Ketone) | 50 |
| 10. | Lemon oil, Italy | 25 |
| 11. | Linalool | 45 |
| 12. | 6-Methoxy-2,6-dimethyloctanal (Calypsone ™) | 20 |
| 13. | Methyl 2,4-dihydroxy-3,6-dimethylbenzoate (Evernyl ™) | 10 |
| 14. | 4-Methyl-2-(2'-methylpropyl)tetrahydro-2H-pyran-4-ol (Florosa ™) | 150 |
| 15. | Orange oil, Brazil | 10 |
| 16. | (10E)-Oxacycloheptadec-10-en-2-one (Ambrettolide ™) | 40 |
| 17. | 4-(5',5',6'-Trimethylbicyclo[2.2.1]hept-2'-yl)cyclohexan-1-ol (Sandela ™) @ 85% in isopropyl myristate | 65 |
| 18. | Tricyclopropyl(1-hydroxy-1-methylethyl)silane | 30 |

Substituting 25/800 parts of dicyclopropyl(1-hydroxy-1-methylethyl)methylsilane in the composition of Example 14 by 30/800 part of tricyclopropyl(1-hydroxy-1-methylethyl)silane preserves the overall patchouli character of the composition, but shifts it more towards the middle note and the dry down. There tricyclopropyl(1-hydroxy-1-methylethyl)silane enhances the overall floralcy by blending particularly well with the Florosa-Cyclohexal-Karanal accord. In effect, the perfume thereby is softened down, gaining volume, depth and intensity.

The invention claimed is:

1. A compound of formula (I)

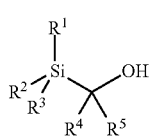

(I)

wherein
R$^1$, R$^2$ and R$^3$ are independently selected from C$_1$-C$_4$ alkyl or C$_3$-C$_4$ cycloalkyl;
with the proviso that at least one of R$^1$, R$^2$ or R$^3$ is selected from C$_3$-C$_4$ alkyl or C$_3$-C$_4$ cycloalkyl;
R$^4$ is methyl or ethyl; and
R$^5$ is methyl or ethyl.

2. A compound of formula (I) according to claim 1 wherein the compound is selected from the group consisting of dicyclopropyl(1-hydroxy-1-methylethyl)methylsilane, tricyclopropyl(1-hydroxy-1-methylethyl)silane, dicyclopropyl(ethyl)(1-hydroxy-1-methylethyl)silane, dicyclopropyl(1-hydroxy-1-methylethyl)isopropylsilane, dicyclopropyl(1-hydroxy-1-methylpropyl)methylsilane, dicyclopropyl(1-ethyl-1-hydroxypropyl)methylsilane, (1-hydroxy-1-methylethyl)(diisopropyl)methylsilane, cyclopropyl(1-hydroxy-1-methylethyl)(diisopropyl)silane, (1-hydroxy-1-methylethyl)triisopropylsilane, (1-hydroxy-1-methylethyl)isobutylisopropyl-methylsilane, di-tert-butyl(1-hydroxy-1-methylethyl)methylsilane and tert-butyl(1-hydroxy-1-methylethyl)dimethylsilane.

3. A fragrance application comprising as odorant at least one compound of formula (I) as defined in claim 1 and a consumer product base.

4. A fragrance application according to claim 3 wherein the consumer product base is selected from fine fragrance, household products, laundry products, body care products, cosmetic and air care products.

5. A fragrance composition comprising at least one compound of formula (I) as defined in claim 1 and a base material.

6. The fragrance composition according to claim 5 comprising at least one compound selected from the group consisting of dicyclopropyl(1-hydroxy-1-methylethyl)methylsilane, tricyclopropyl(1-hydroxy-1-methylethyl)silane, dicyclopropyl(ethyl)(1-hydroxy-1-methylethyl)silane, dicyclopropyl(1-hydroxy-1-methylethyl)isopropylsilane, dicyclopropyl(1-hydroxy-1-methylpropyl)methylsilane, dicyclopropyl(1-ethyl-1-hydroxypropyl)methylsilane, (1-hydroxy-1-methylethyl)(diisopropyl)methylsilane, cyclopropyl(1-hydroxy-1-methylethyl)(diisopropyl)silane, (1-hydroxy-1-methylethyl)triisopropylsilane, (1-hydroxy-1-methylethyl)(isobutyl)isopropyl(methyl)silane, di-tert-butyl(1-hydroxy-1-methylethyl)methylsilane and tert-butyl(1-hydroxy-1-methylethyl)dimethylsilane.

7. A method of improving, enhancing or modifying a consumer product base by addition thereto of an olfactory acceptable amount of at least one compound of formula (I) as defined in claim 1.

8. The method of claim 7 wherein the compound is selected from the group consisting of dicyclopropyl(1-hydroxy-1-methylethyl)methylsilane, tricyclopropyl(1-hydroxy-1-methylethyl)silane, dicyclopropyl(ethyl)(1-hydroxy-1-methylethyl)silane, dicyclopropyl(1-hydroxy-1-methylethyl)isopropylsilane, dicyclopropyl(1-hydroxy-1-methylpropyl)methylsilane, dicyclopropyl(1-ethyl-1-hydroxypropyl)methylsilane, (1-hydroxy-1-methylethyl)-(diisopropyl)methylsilane, cyclopropyl(1-hydroxy-1-methylethyl)(diisopropyl)silane, (1-hydroxy-1-methylethyl)triisopropylsilane, (1-hydroxy-1-methylethyl)(isobutyl)isopropyl(methyl)silane, di-tert-butyl(1-hydroxy-1-methylethyl)methylsilane and tert-butyl(1-hydroxy-1-methylethyl)dimethylsilane.

9. A fragrance application comprising as odorant at least one compound as defined in claim 2 and a consumer product base.

10. The fragrance application according to claim 9 wherein the consumer product base is selected from fine fragrance, household products, laundry products, body care products, cosmetic and air care products.

* * * * *